(12) United States Patent
Thompson et al.

(10) Patent No.: US 6,728,576 B2
(45) Date of Patent: Apr. 27, 2004

(54) NON-CONTACT EKG

(75) Inventors: David L. Thompson, Andover, MN (US); Suzanne L. Wilson, Campbellville (CA)

(73) Assignee: Medtronic, Inc., Minneapolis, MN (US)

( * ) Notice: Subject to any disclaimer, the term of this patent is extended or adjusted under 35 U.S.C. 154(b) by 305 days.

(21) Appl. No.: 10/004,045

(22) Filed: Oct. 31, 2001

(65) Prior Publication Data

US 2003/0083714 A1 May 1, 2003

(51) Int. Cl.[7] .................... A61N 1/372; A61N 1/375
(52) U.S. Cl. ............................................. 607/30
(58) Field of Search ................... 128/903; 600/509, 600/513; 9/9, 30, 32, 37

(56) References Cited

U.S. PATENT DOCUMENTS

| | | | |
|---|---|---|---|
| 3,983,867 A | 10/1976 | Case ................. 128/2.06 G |
| 4,023,565 A | 5/1977 | Ohlsson ............. 128/2.06 B |
| 4,082,086 A | 4/1978 | Page et al. .......... 128/2.06 E |
| 4,170,227 A | 10/1979 | Feldman et al. .......... 128/704 |
| 4,263,919 A | 4/1981 | Levin .................... 128/708 |
| 4,310,000 A | 1/1982 | Lindemans .......... 128/419 PG |
| 4,313,443 A | 2/1982 | Lund .................... 128/642 |
| 4,476,868 A | 10/1984 | Thompson .......... 128/419 PG |
| 4,593,702 A | 6/1986 | Kepski et al. ............. 128/696 |
| 4,674,508 A | 6/1987 | DeCote ............... 128/419 PT |
| 4,729,376 A | 3/1988 | DeCote, Jr. ........... 128/419 PT |
| 4,919,136 A | 4/1990 | Alt ..................... 128/419 P |
| 4,957,109 A | 9/1990 | Groeger et al. ............ 128/640 |
| 4,981,141 A | 1/1991 | Segalowitz ............... 128/696 |
| 5,007,427 A | 4/1991 | Suzuki et al. .............. 128/659 |
| 5,027,824 A | 7/1991 | Dougherty et al. ......... 128/702 |
| 5,052,388 A | 10/1991 | Sivula et al. .......... 128/419 PG |
| 5,111,818 A | 5/1992 | Suzuki et al. .............. 128/644 |
| 5,113,869 A | 5/1992 | Nappholz et al. ............ 128/696 |
| 5,168,871 A | 12/1992 | Grevious ............... 128/419 PT |
| 5,307,818 A | 5/1994 | Segalowitz ............... 128/696 |
| 5,331,966 A | 7/1994 | Bennett et al. ............. 128/696 |
| 5,345,362 A | 9/1994 | Winkler .................. 361/681 |
| 5,467,773 A | 11/1995 | Bergelson et al. .......... 128/709 |
| 5,511,553 A | 4/1996 | Segalowitz ............... 128/696 |
| 5,513,645 A | 5/1996 | Jacobson et al. ........... 128/710 |
| 5,560,368 A | 10/1996 | Berger .................... 128/703 |
| 5,573,012 A | 11/1996 | McEwan .................. 128/782 |
| 5,634,468 A | 6/1997 | Platt et al. ................ 128/696 |
| 5,669,393 A | 9/1997 | Faisandier ................ 128/710 |
| 5,752,976 A | 5/1998 | Duffin et al. ............... 607/32 |
| 5,766,133 A | 6/1998 | Faisandier ................ 600/509 |
| 5,766,708 A | 6/1998 | Panizza .................. 428/36.1 |
| 5,772,586 A | 6/1998 | Heinonen et al. ........... 600/300 |
| 5,876,353 A | 3/1999 | Riff ...................... 600/547 |
| 5,957,861 A | 9/1999 | Combs et al. ............. 600/547 |
| 5,966,090 A | 10/1999 | McEwan .................. 342/27 |
| 5,986,600 A | 11/1999 | McEwan .................. 342/28 |

(List continued on next page.)

FOREIGN PATENT DOCUMENTS

| | | | | |
|---|---|---|---|---|
| EP | 1134003 A2 | * | 9/2001 | ......... A61N/1/372 |
| WO | WO 01/16607 | | 3/2001 | |

*Primary Examiner*—Carl Layno
(74) *Attorney, Agent, or Firm*—Girma Wolde-Michael

(57) ABSTRACT

A non-tissue contacting electrode system senses physiologic signals from a patient during implant and/or followup of an implantable medical device (IMD) via an external programmer or other monitoring instrument. These sensing systems are electrically connected to the circuitry of the external device and detect cardiac depolarization waveforms displayable as electrocardiographic tracings on the instrument screen when the programming head is positioned above an implanted pacemaker (or other implanted device) so equipped with a non-tissue contacting electrode system. The structure and system provide an enhanced capability for detecting and gathering physiological signals from a patient with minimally invasive patient contact.

17 Claims, 9 Drawing Sheets

U.S. PATENT DOCUMENTS

| | | | |
|---|---|---|---|
| 5,987,352 A | 11/1999 | Klein et al. | 600/509 |
| 6,083,248 A | 7/2000 | Thompson | 607/30 |
| 6,115,628 A | 9/2000 | Stadler et al. | 600/517 |
| 6,115,630 A | 9/2000 | Stadler et al. | 600/521 |
| 6,128,526 A | 10/2000 | Stadler et al. | 600/517 |
| 6,200,265 B1 | 3/2001 | Walsh et al. | 600/300 |
| 6,292,698 B1 | 9/2001 | Duffin et al. | 607/32 |
| 6,650,941 B2 * | 11/2003 | Ferek-Petric | 607/30 |

* cited by examiner

NON-CONTACT EKG

FIELD OF THE INVENTION

The present invention relates generally to implantable medical devices such as pacemakers and more particularly to a method and apparatus to acquire electrocardiographic data, waveform tracings, and other physiologic data displayable by a programmer from an implantable medical device patient without the need for, or use of, surface (skin) contacting electrodes.

BACKGROUND OF THE INVENTION

The electrocardiogram (ECG) is commonly used in medicine to determine the status of the electrical conduction system of the human heart. As practiced the ECG recording device is commonly attached to the patient via ECG leads connected to pads arrayed on the patient's body so as to generate a recording that displays the cardiac waveforms in any one of 12 possible vectors.

The history of the ECG dates back to 1842 when the Italian physicist, Carlo Matteucci discovered that each heartbeat was accompanied by a detectable electric signal. In 1878, two British physiologists, John Burden Sanderson and Frederick Page, determined that the heart signal consisted of, at least, two phases, the QRS (ventricular depolarization) and the repolarization or T-wave. It was not until 1893, however, that Willem Einthoven introduced the term 'electrocardiogram' at a meeting of the Dutch Medical Association, although he later disavowed he was the originator of the term.

Einthoven may, however, be called the father of electrocardiography, since he won the Nobel Prize for his achievements in 1924. It was he who finally dissected a heart and named all of the cardiac waveforms (P, Q, R, S, T) that commonly appear on an ECG tracing from a 'normal' person.

Einthoven and other medical practitioners of that time were aware of only three vectors (I, II, and III) that are achieved by placement of the ECG electrodes on specific body sites. The remaining nine sites were discovered later in the twentieth century. In 1938, American Heart Association and the Cardiac Society of Great Britain defined the standard positions (I–III) and wiring of the chest leads V1–V6. The 'V' stands for voltage. Finally, in 1942, Emanuel Goldberger added the augmented limb leads aVR, aVL and aVF to Einthoven's three limb leads and the six chest leads thereby creating the 12-lead electrocardiogram that is routinely used today for cardiac diagnostic purposes.

Since the implantation of the first cardiac pacemaker, implantable medical device technology has advanced with the development of sophisticated, programmable cardiac pacemakers, pacemaker-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) that currently requires externally attached electrodes and the electrogram (EGM) that requires implanted pacing leads. The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. Acquisition and use of ECG tracing(s), on the other hand, has generally been limited to the use of an external ECG recording machine attached to the patient via surface electrodes of one sort or another.

The aforementioned ECG systems that utilize detection and analysis of the PQRST complex are all dependent upon the spatial orientation and number of electrodes available in or around the heart to pick up the depolarization wave front.

As the functional sophistication and complexity of implantable medical device systems increased over the years, it has become increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available that transmit a digitized electrical signal to display electrical cardiac activity (e.g., an ECG, EGM, or the like) for storage and/or analysis by an external device. The surface ECG, in fact, has remained the standard diagnostic tool since the very beginning of pacing and remains so today.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure used to determine cardiac status prior to implanting a pacing system; thereafter, the physician will normally use an ECG available through the programmer to check the pacemaker's efficacy after implantation. Such ECG tracings are placed into the patient's records and used for comparison to more recent tracings. It must be noted, however, that whenever an ECG recording is required (whether through a direct connection to an ECG recording device or to a pacemaker programmer), external electrodes and leads must be used.

Another possible approach is described in pending applications Ser. No. 09/749,169, Leadless Fully Automatic Pacemaker Follow-Up filed Dec. 27, 2000; Ser. No. 09/696,365, Multilayer Ceramic Electrodes For Sensing Cardiac Depolarization Signals, filed Oct. 25, 2000; Ser. No. 09/697,438, Surround Shroud Connector and Electrode Housings For A Subcutaneous Electrode Array and Leadless ECGs, filed Oct. 26, 2000; Ser. No. 09/703,152, Subcutaneous Spiral Electrode For Sensing Electrical Signals of the Heart, filed Oct. 31, 2000; Ser. No. 09/736,640, Atrial Aware VVI—A Method For Atrial Synchronous Ventricular (VDD/R) Pacing Using the Subcutaneous Electrode Array and a Standard Pacing Lead, filed Dec. 14, 2000; Ser. No. 09/850,331, Subcutaneous Sensing Feedthrough/ Electrode Assembly, filed May 7, 2000; and Ser. No. 09/721,275, System And Method For Deriving a Virtual ECG IR EGM Signal, filed Nov. 22, 2000; whereby a subcutaneous leadless pseudo EKG is sensed from the can of the IMD and transmitted to an external programmer via telemetry. The '169, '365, '438, '152, '640, '331, and '275 applications are incorporated herein by reference in their entireties.

In the art known to the inventors and current practice there are noticeable limitations. For example, electrocardiogram analysis performed using existing external or body surface ECG systems can be limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration or motion. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the pacemaker follow-up session.

Other art relating to subcutaneous leadless pseudo EKG concept deals with generating a pseudo EKG signal via pulse generator externalized electrodes and signal conditioning electronics. This method of EKG acquisition is rapid, does not require electrode positioning and does not require patient disrobing. However, there is substantial increase in device cost, increased circuit complexity, increased IMD device size, and an IMD aesthetic degradation.

Prior art describes systems to monitor electrical activity of the human heart for diagnostic and related medical purposes. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems which combine surface EKG signals for artifact rejection.

The primary implementation for multiple electrode systems in the prior art is vector cardiography from ECG signals taken from multiple chest and limb electrodes. This is a technique whereby the direction of depolarization of the heart is monitored, as well as the amplitude, generally similar to the disclosure in U.S. Pat. No. 4,121,576 to Greensite.

Numerous body surface ECG monitoring electrode systems have been employed in the past in detecting the ECG and conducting vector cardiographic studies. For example, U.S. Pat. No. 4,082,086 to Page, et al., discloses a four electrode orthogonal array that may be applied to the patient's skin both for convenience and to ensure the precise orientation of one electrode to the other. U.S. Pat. No. 3,983,867 to Case describes a vector cardiography system employing ECG electrodes disposed on the patient in normal locations and a hex axial reference system orthogonal display for displaying ECG signals of voltage versus time generated across sampled bipolar electrode pairs.

U.S. Pat. No. 4,310,000 to Lindemans and U.S. Pat. Nos. 4,729,376 and 4,674,508 to DeCote, incorporated herein by reference, disclose the use of a separate passive sensing reference electrode mounted on the pacemaker connector block or otherwise insulated from the pacemaker case in order to provide a sensing reference electrode which is not part of the stimulation reference electrode and thus does not have residual after-potentials at its surface following delivery of a stimulation pulse.

Moreover, in regard to subcutaneously implanted EGM electrodes, the aforementioned Lindemans U.S. Pat. No. 4,310,000 discloses one or more reference-sensing electrode positioned on the surface of the pacemaker case as described above. U.S. Pat. No. 4,313,443 issued to Lund describes a subcutaneously implanted electrode or electrodes for use in monitoring the ECG.

Finally, U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

SUMMARY OF THE INVENTION

The present invention encompasses a non-tissue contacting electrode system for the sensing of physiologic signals from a patient that may be implemented during the implant and/or follow-up of an implantable medical device (IMD) via an external programmer or other monitoring instrument. These sensing systems are electrically connected to the circuitry of the external device and detect cardiac depolarization waveforms displayable as electrocardiographic tracings on the instrument screen when the programming head is positioned above an implanted device, such as a pacemaker, so equipped with a non-tissue contacting electrode system.

The present invention provides a method and apparatus that may be implemented for use in conjunction with the aforementioned medical devices to provide an enhanced capability of detecting and gathering electrical cardiac signals via non-tissue contacting sensors.

The present invention enables the physician or medical technician to perform follow-up regiments that, in turn, eliminate the time it takes to attach external adhesive electrodes to the patient's skin. Such timesavings can reduce the cost of follow-up, as well as making it possible for the physician or medical technician to see more patients during each day. Though not limited to these, other uses include: Holter monitoring with event storage, arrhythmia detection and monitoring, capture detection, ischemia detection and monitoring (S-T elevation and depression on the ECG), changes in QT interval (i.e., QT variability), transtelephonic monitoring, web-enabled remote patient management and chronic remote patient care.

DETAILED DESCRIPTION OF THE DRAWINGS

Figure 1:
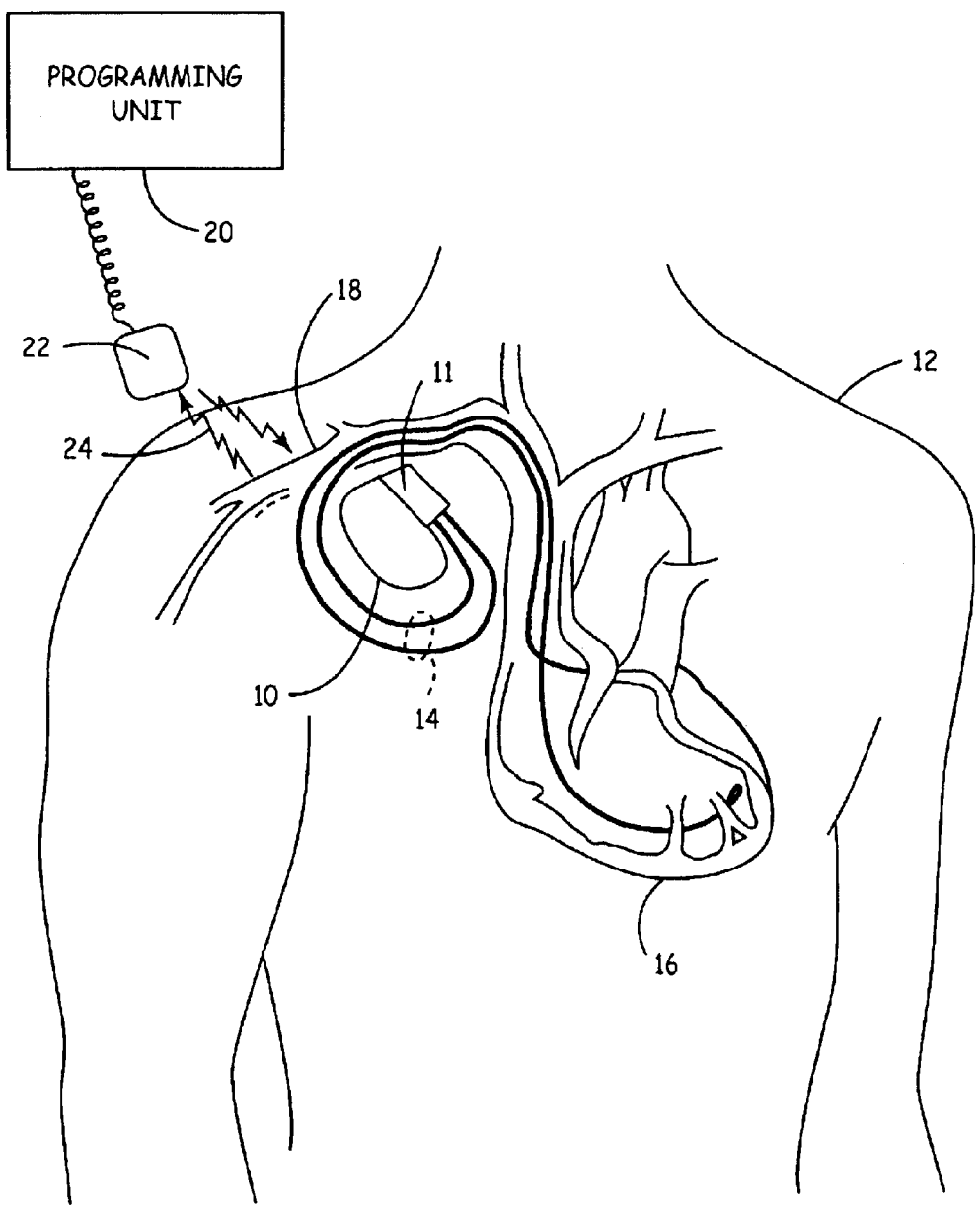
FIG. 1 is an illustration of a body-implantable device system in accordance with one embodiment of the invention, including a hermetically sealed device implanted in a patient and an external programming unit.

FIG. 1 is an illustration of an implantable medical device system adapted for use in accordance with the present invention. The medical device system shown in FIG. 1 includes an implantable device 10—a pacemaker in this embodiment—which has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide a communication link between two physically separated components, such as may occur during transtelephonic monitoring.

Also depicted in FIG. 1 is an external programming unit 20 for non-invasive communication with implanted device 10 via uplink and downlink communication channels 24, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device, such that one or more antennae within the head can send RF signals to, and receive RF signals from, an antenna disposed within the hermetic enclosure of the implanted device or disposed within the connector block of the device, in accordance with common practice in the art.

Figure 2:
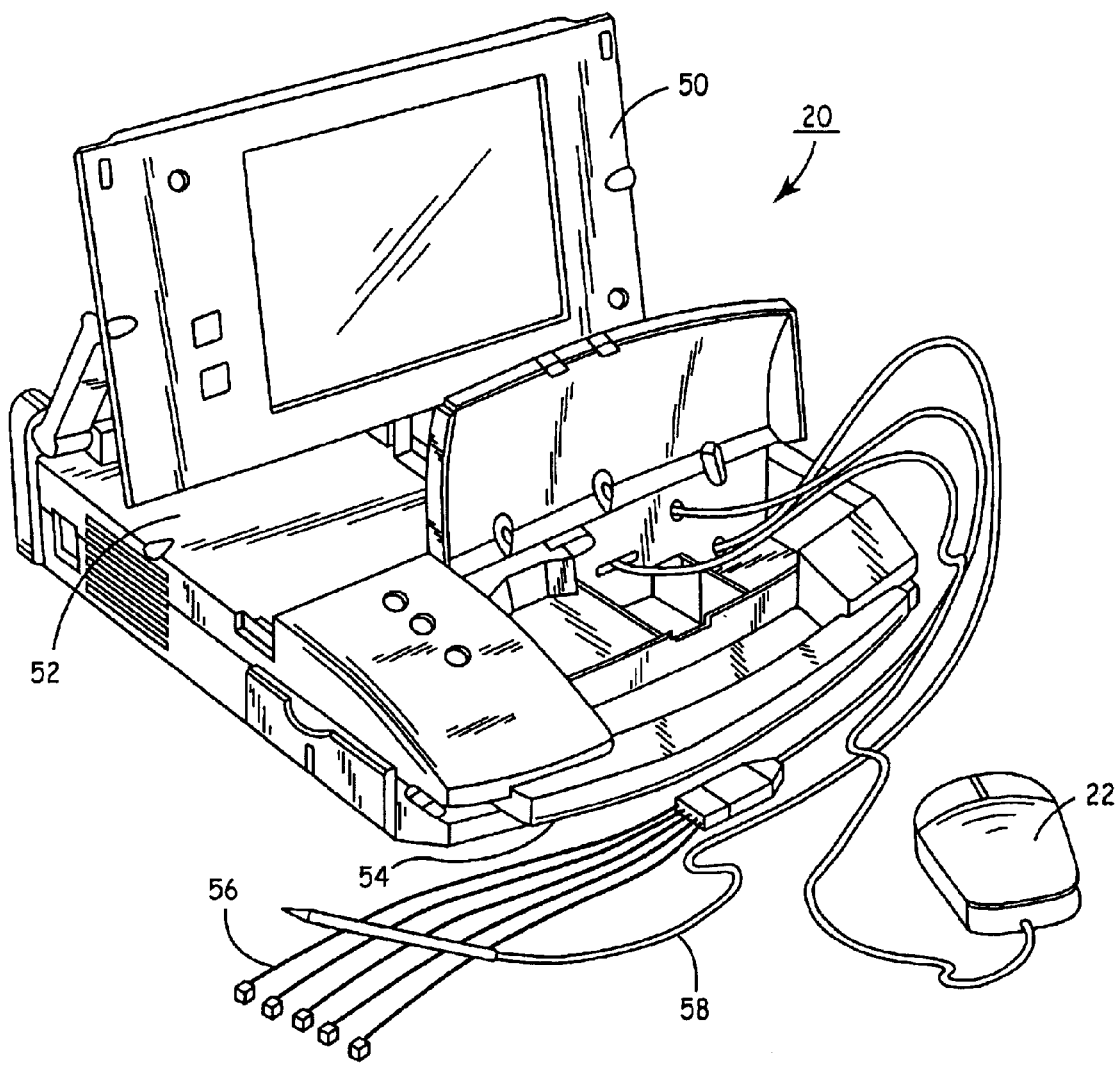
FIG. 2 is a view of the external programming unit of FIG. 1.

In FIG. 2, there is shown a perspective view of programming unit 20 in accordance with the presently disclosed invention. Internally, programmer 20 includes a processing unit (not shown in the Figures) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 2, programmer 20 comprises an outer housing 52, which is preferably made of thermal plastic or another suitably rugged yet relatively lightweight material. A carrying handle, designated generally as 54 in FIG. 2, is integrally formed into the front of housing 52. With handle 54, programmer 20 can be carried like a briefcase.

An articulating display screen 50 is disposed on the upper surface of housing 52. Display screen 50 folds down into a closed position (not shown) when programmer 20 is not in use, thereby reducing the size of programmer 20 and protecting the display surface of display 50 during transportation and storage thereof.

A floppy disk drive is disposed within housing 52 and is accessible via a disk insertion slot (not shown). A hard disk drive is also disposed within housing 52, and it is contemplated that a hard disk drive activity indicator, (e.g., an LED, not shown) could be provided to give a visible indication of hard disk activation.

Those with ordinary skill in the art would know that it is often desirable to provide a means for determining the status of the patient's conduction system. Normally, programmer 20 is equipped with external ECG leads 54. It is these leads which are rendered redundant by the present invention.

In accordance with the present invention, programmer 20 is equipped with an internal printer (not shown) so that a hard copy of a patient's ECG or of graphics displayed on the programmer's display screen 50 can be generated. Several types of printers, such as the AR-100 printer available from General Scanning Co., are known and commercially available.

In the perspective view of FIG. 2, programmer 20 is shown with articulating display screen 50 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

Display screen 50 is operatively coupled to the computer circuitry disposed within housing 52 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
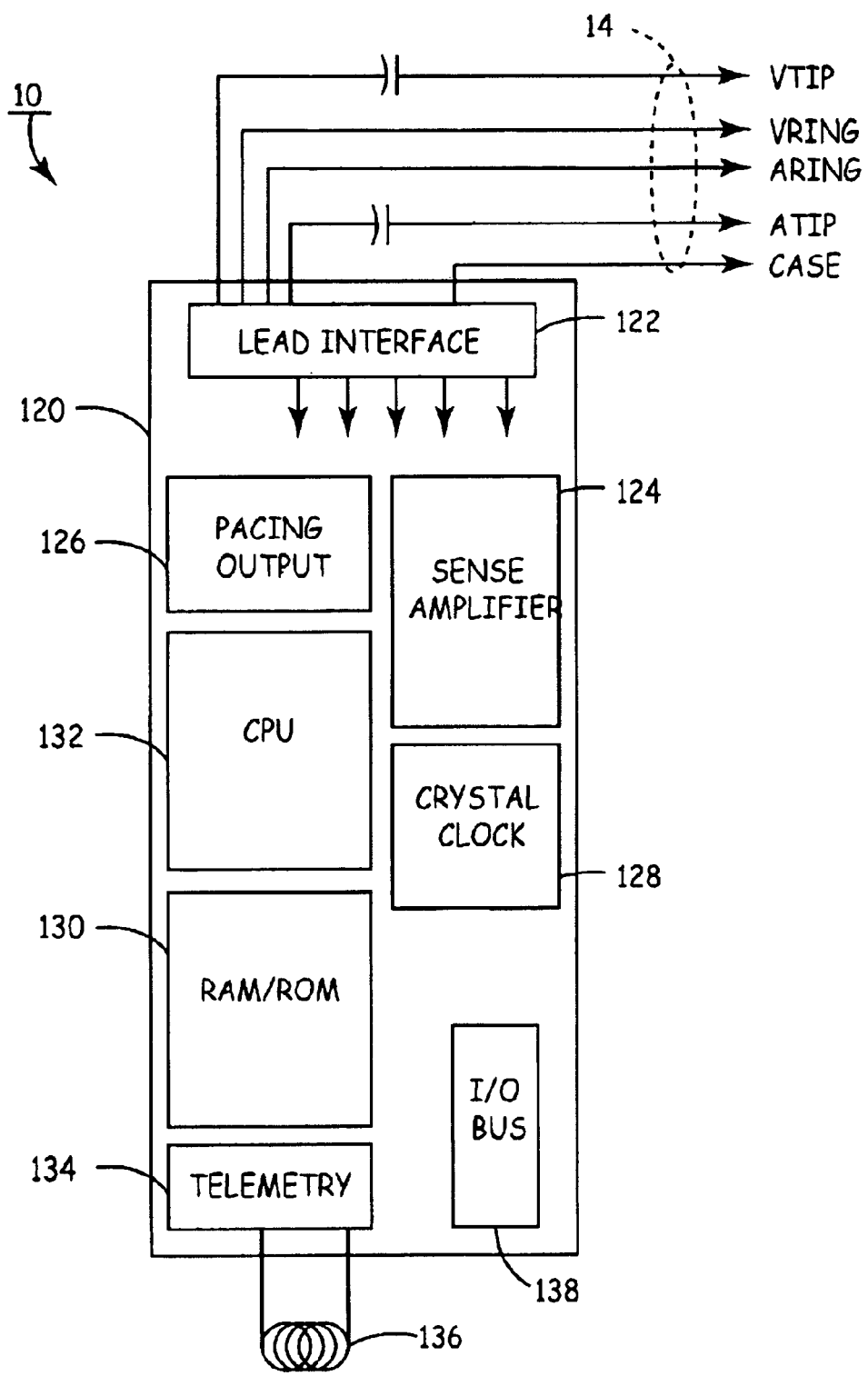
FIG. 3 is a block diagram of the body-implantable system of FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 120 for controlling the device's pacing and sensing functions. The circuitry associated with stimulation control circuit 120 may be of conventional design, in accordance, for example, with what is disclosed U.S. Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 120 in FIG. 3 includes sense amplifier circuitry 124, stimulating pulse output circuitry 126, a crystal clock 128, a random-access memory and read-only memory (RAM/ROM) unit 130, and a central processing unit (CPU) 132, all of which are well-known in the art.

Pacemaker 10 also includes internal communication circuit 134 so that it is capable of communicating with external programmer/control unit 20, as described in FIG. 2 in greater detail.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 122 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 124 and stimulating pulse output circuit 126, in accordance with common practice, such that cardiac electrical signals may be conveyed to sensing circuitry 124, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 120 includes central processing unit 132 which may be an off-the-shelf programmable microprocessor or micro controller, but in the present invention is a custom integrated circuit. Although specific connections between CPU 132 and other components of stimulation control circuit 120 are not shown in FIG. 3, it will be apparent to those of ordinary skill in the art that CPU 132 functions to control the timed operation of stimulating pulse output circuit 126 and sense amplifier circuit 124 under control of programming stored in RAM/ROM unit 130. It is believed that those of ordinary skill in the art will be familiar with such an operative arrangement.

With continued reference to FIG. 3, crystal oscillator circuit 128, in the presently preferred embodiment a 32,768-Hz crystal controlled oscillator, provides main timing clock signals to stimulation control circuit 120. Again, the lines over which such clocking signals are provided to the various timed components of pulse generator 10 (e.g., microprocessor 132) are omitted from FIG. 3 for the sake of clarity.

It is to be understood that the various components of pulse generator 10 depicted in FIG. 3 are powered by means of a battery (not shown) which is contained within the hermetic enclosure of pacemaker 10, in accordance with common practice in the art. For the sake of clarity in the Figures, the battery and the connections between it and the other components of pulse generator 10 are not shown.

Stimulating pulse output circuit 126, which functions to generate cardiac stimuli under control of signals issued by CPU 132, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 124, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 132 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 134 in pacemaker 10, and an associated communication subsystem in external unit 20.

Figure 4:
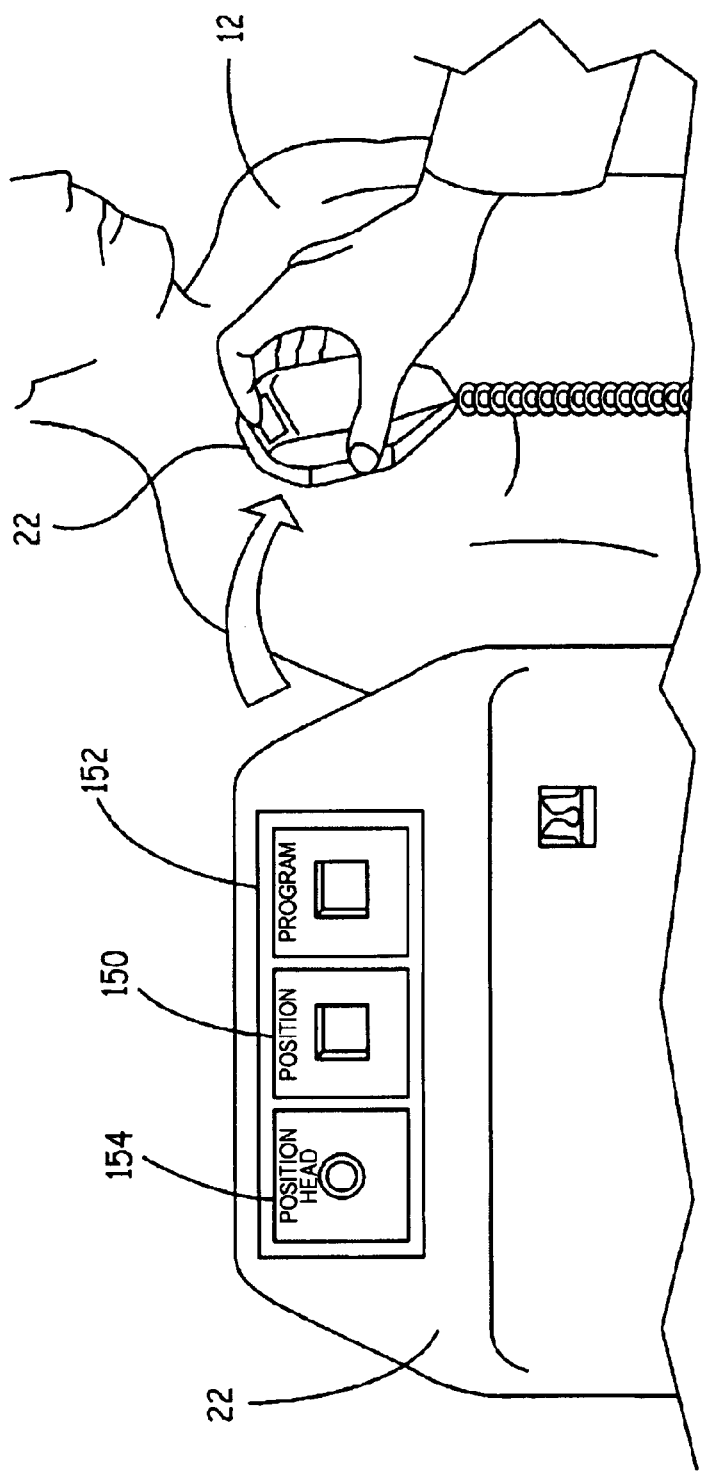
FIG. 4 is a view of the external programming unit of FIG. 1 being used to program and/or interrogate the implanted device of FIG. 1.

The programming head 22 depicted in FIG. 4 possesses a pair of push button switches 150 and 152 labeled INTERROGATE and PROGRAM respectively. In use, the physician places the programmer head over IMD 20 and depresses one or the other of the two buttons as shown in FIG. 4, and those depressed buttons control the overall function of the programmer circuitry of FIG. 2. Communication channel function and status to IMD 10 (not shown) is indicated via LED 54.

Figure 5:
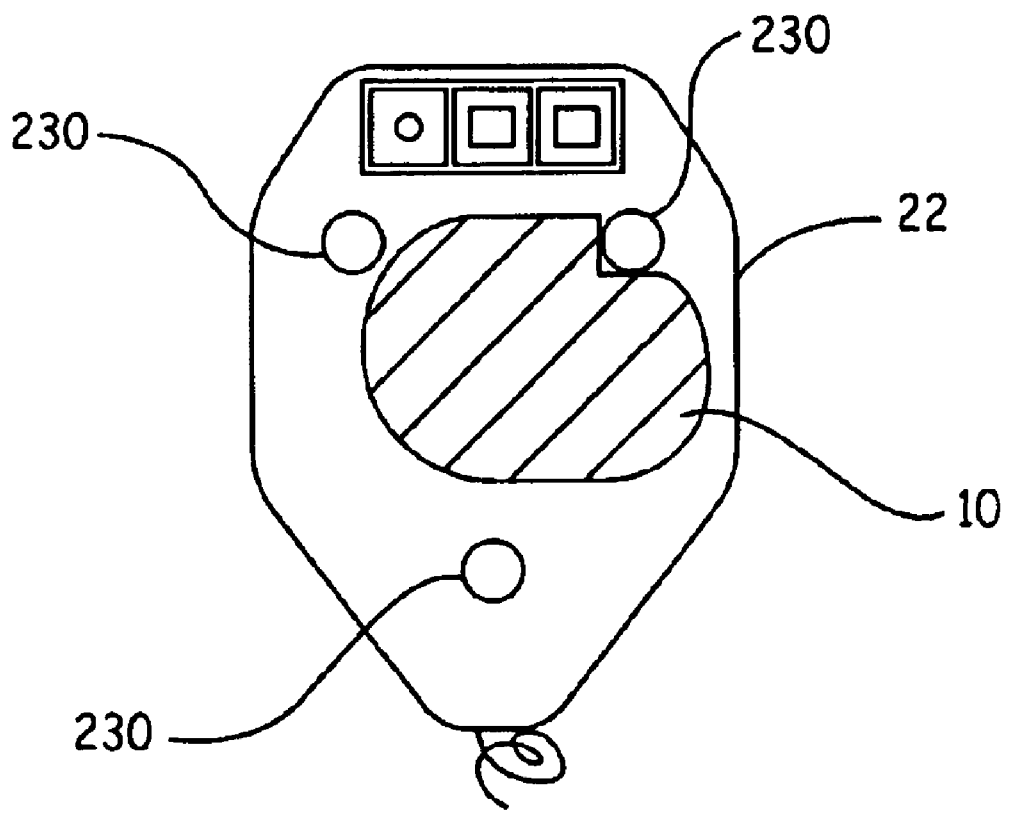
FIG. 5 is a diagram of the communication head from the programmer unit of FIG. 2 encompassing a capacitive pickup electrode sensor.

FIG. 5 depicts programming head 22 with 3 electrodes 230 shown positioned on the surface facing the patient. Note that 1 to 3 electrodes 230 may be used with this invention. IMD 10 is shown in relief under the programming head 22, positioned to receive and transmit RF telemetry from/to IMD 10. Electrodes 230 are as substantially described in PCT application WO 01/16607, ELECTRIC FIELD SENSOR, by Brun del Re, et al, incorporated by reference in its entirety. The Brun del Re '607 application describes an electric field sensor employing a capacitive pickup electrode in a voltage divider network connected to a body emanating an electric field. The system is relatively insensitive to variations in the separation gap between electrode and body, reducing sensor motion artifacts in the output signal and stabilizing its low frequency response. The pick-up electrode may be positioned at a "stand off" location, spaced from intimate contact with the surface of the body. Human body-generated electrical signals may be acquired without use of conductive gels and suction-based electrodes, without direct electrical contact to the body and even through layers of clothing. One electrode 230 may be used as a signal pickup, however, optionally, two or more electrodes 230 may be used to differentially pickup the physiologic signal. Also by using multiple electrodes, the larger of two or more signals may be selected for an increased signal to noise ratio. Alternatively, sensor(s) 230 may be attached to the programmer 20 via a separate cable such as 56 of FIG. 2. Optionally, sensor(s) 230 may be connected to the patient via an adhesive strip and cable 56.

Figure 6:
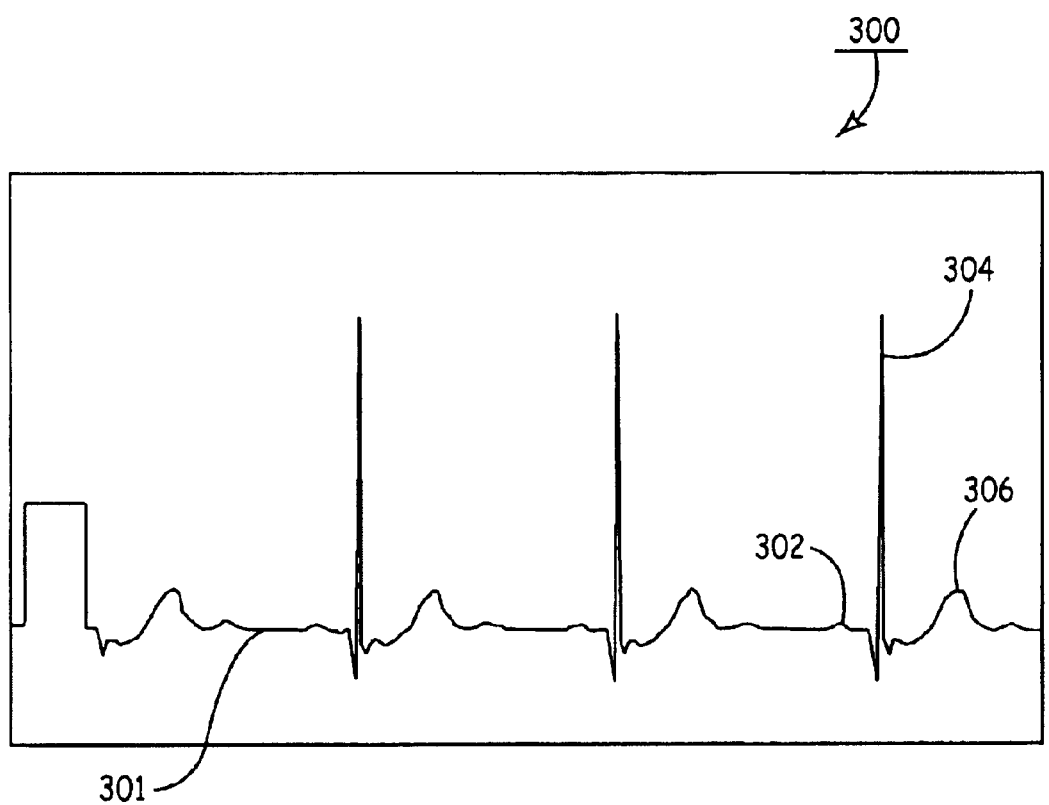
FIG. 6 is a display of an ECG tracing from a capacitive, non-tissue contacting sensor.

FIG. 6 displays an ECG tracing 301, superimposed upon a grid 300, taken during an acute study from a human patient utilizing the sensor 230 of FIG. 5, showing a p-wave 302, a QRS complex 304, and a T-wave 306. These signals may be used to enable the follow-up clinician or technician to rapidly and accurately determine IMD function vis-a-vis proper sensing, atrial and ventricular capture, A-V delay function, rate response parameters, multi-site pacing parameters and other functions/operations as per described in the hereinabove mentioned, and incorporated by reference, '169 pending application.

Figure 7:
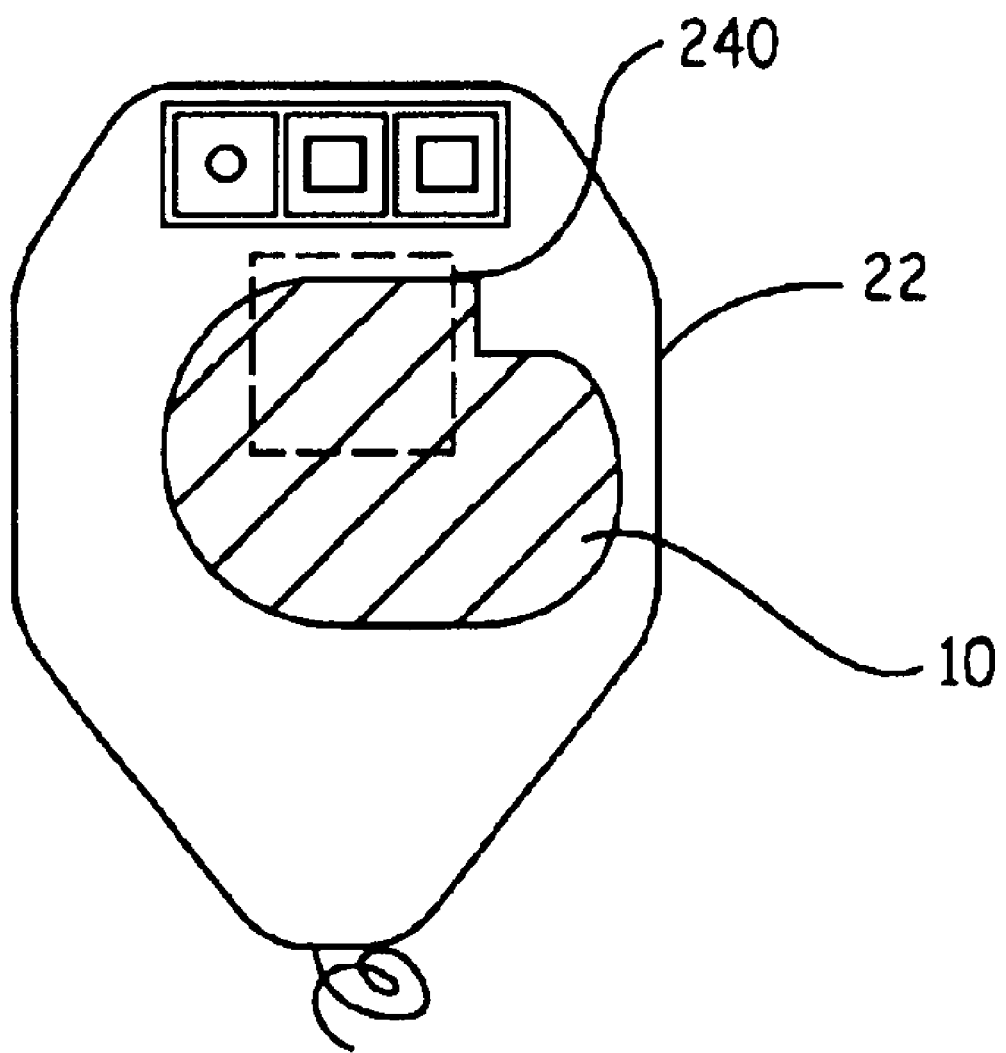
FIG. 7 is a diagram of the communication head from the programmer unit of FIG. 2 encompassing a non-acoustic pulse-echo radar monitor sensor.

FIG. 7 depicts programming head 22 with a sensor 240 positioned on the surface facing the patient. IMD 10 is shown in relief under the programming head 22, positioned correctly for the reception and transmission of RF telemetry from/to IMD 10. Sensor 240 is as substantially described in U.S. Pat. Nos. 5,573,012, 5,966,090 and 5,986,600 by McEwan, incorporated by reference in their entireties. The McEwan '012, '090, and '600 patents describe a non-acoustic pulse-echo radar monitor, employed in a repetitive mode, whereby a large number of reflected pulses are averaged to produce a voltage that corresponds to the heart motion. The antenna used in this monitor generally comprises two flat copper foils, thus permitting the antenna to be housed in a substantially flat housing. It further uses a dual time constant to reduce the effect of gross sensor-to-surface movement. The monitor detects the movement of one or more internal body parts, such as the heart, lungs, arteries, and vocal chords, and includes a pulse generator for simultaneously inputting a sequence of pulses to a transmit path and a gating path. The pulses transmitted along the transmit path drive an impulse generator and provide corresponding transmit pulses that are applied to a transmit antenna. The gating path includes a range delay generator which generates timed gating pulses. The timed gating pulses cause the receive path to selectively conduct pulses reflected from the body parts and received by a receive antenna. The monitor output potential can be separated into a cardiac output indicative of the physical movement of the heart, and a pulmonary output indicative of the physical movement of the lung. Alternatively, the sensor 240 may be attached to programmer 20 via a separate cable such as 56 of FIG. 2. Optionally, the sensor 240 may be connected to the patient via an adhesive strip and cable 56. Further, sensor 240 may be attached to programmer 20 with signal pickup when the patient is positioned within 1 meter in front of programmer 20.

Figure 8:
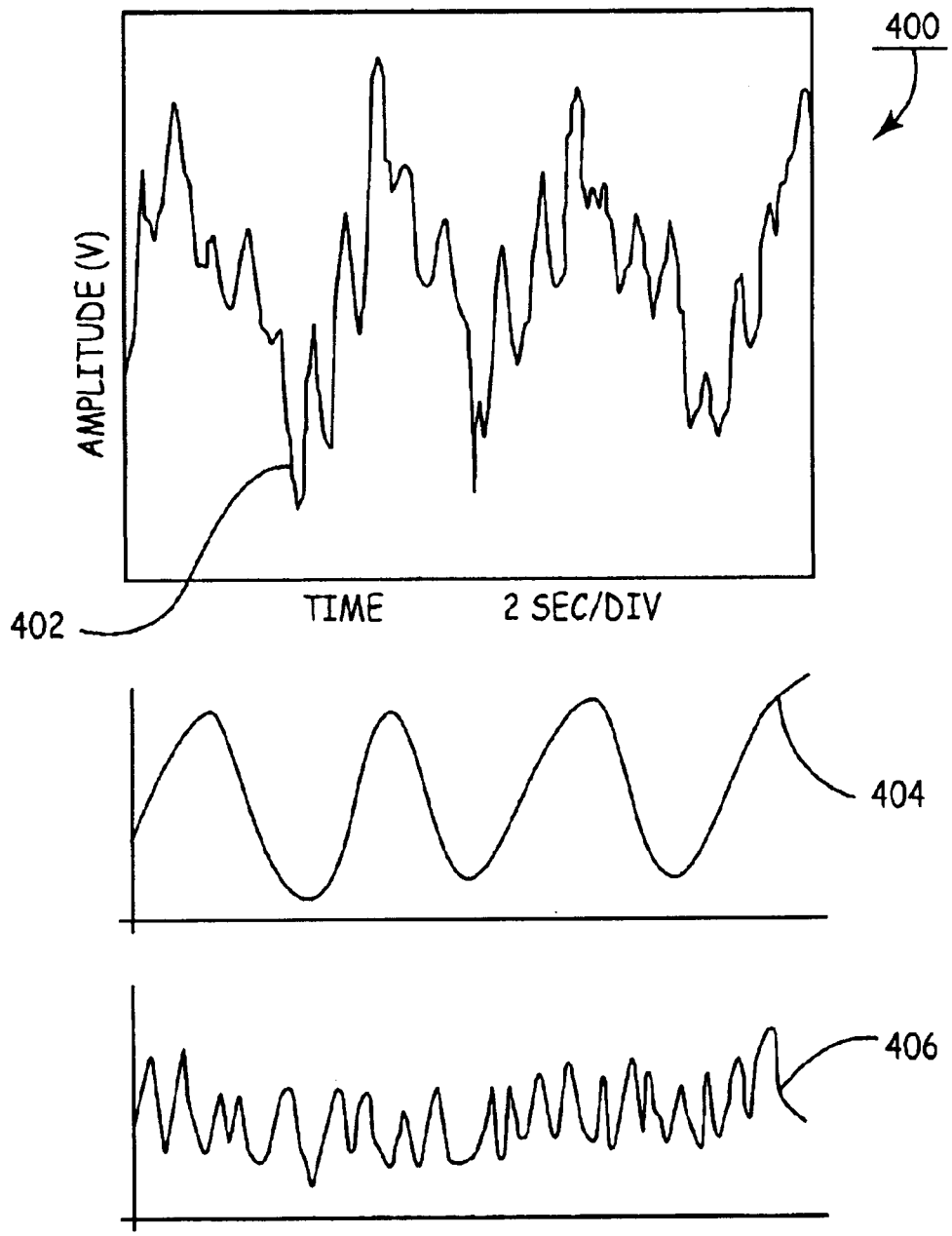
FIG. 8 is a display of an ECG tracing from a non-acoustic, pulse-echo radar, non-tissue contacting sensor.

FIG. 8 displays a physiologic waveform 402, superimposed upon a grid 400, taken during an acute study from a human patient utilizing the sensor 240 of FIG. 7. The composite signal 402 is low pass filtered to remove the cardiac signal component with the respiration signal 404 remaining. Respiration signal 404 consists of respiration rate (frequency of breathing) and tidal volume (amplitude). This signal may be used by the follow-up clinician or technician to monitor and/or optimize the performance of respiration-based rate responsive pacemakers, such as substantially described in U.S. Pat. No. 4,919,136 to Alt, incorporated herein by reference in its entirety. Additionally, this signal may be used to monitor and/or optimize emphysema, edema or CHF patients as described in U.S. Pat. Nos. 5,957,861 to Combs, et al, and U.S. Pat. No. 5,876,353 to Riff, incorporated herein by reference in their entireties.

The composite signal 402 is high pass filtered to remove the tidal volume signal component with the cardiac signal 406 remaining. The cardiac component may be used to enable the follow-up clinician or technician to rapidly and accurately determine IMD function vis-a-vis proper sensing, atrial and ventricular capture, A-V delay function, rate response parameters, multi-site pacing parameters and other functions/operations as per described in the hereinabove mentioned, and incorporated by reference, '169 pending application.

The cardiac signal 406 may be additionally used to detect and assess acute ischemia via ST segment elevation and depression such as described in U.S. Pat. Nos. 6,115,628, 6,115,630 and 6,128,526, all to Stadler et al. The Stadler et al. '628, '630, and '526 patents are incorporated herein by reference in their entireties.

Cardiac signal 406 may additionally be used to measure and assess QT variability as described in U.S. Pat. No. 5,560,368 to Berger. The Berger '368 patent is herein incorporated by reference in its entirety.

The cardiac signal 406 may additionally be used to remotely monitor and transmit EKG signals from a patient's home without wrist electrodes or tape-on electrodes as described in U.S. Pat. No. 5,467,773 to Bergelson, et al. The Bergelson '773 patent is incorporated herein by reference in its entirety. These signals may be transmitted via cellular means or, alternatively, by the Internet to a remote monitoring station as described in U.S. Pat. Nos. 5,752,976 and, 6,292,698 to Duffin et al., U.S. Pat. No. 6,083,248 to Thompson; U.S. patent application Ser. No. 09/348,506, System For Remote Communication With a Medical Device to Ferek-Petric, filed Jul. 7, 1999; U.S. Provisional Application No. 09/765,484, System and Method of Communicating Between an Implantable Medical Device and a Remote Computer System or Health Care Provider to Haller, et al, filed Jan. 18, 2001; U.S. Pat. No. 5,772,586, Method For Monitoring the Health of a Patient to Heinonen; and U.S. Pat. No. 5,113,869, Implantable Ambulatory Electrocardiogram Monitor to Nappholz. The Duffin '976, '698; Thompson '248; Heinonen '586; and Nappholz '869 patents and Ferek-Petric '506 and Haller '484 applications are herein incorporated by reference in their entireties.

Figure 9:
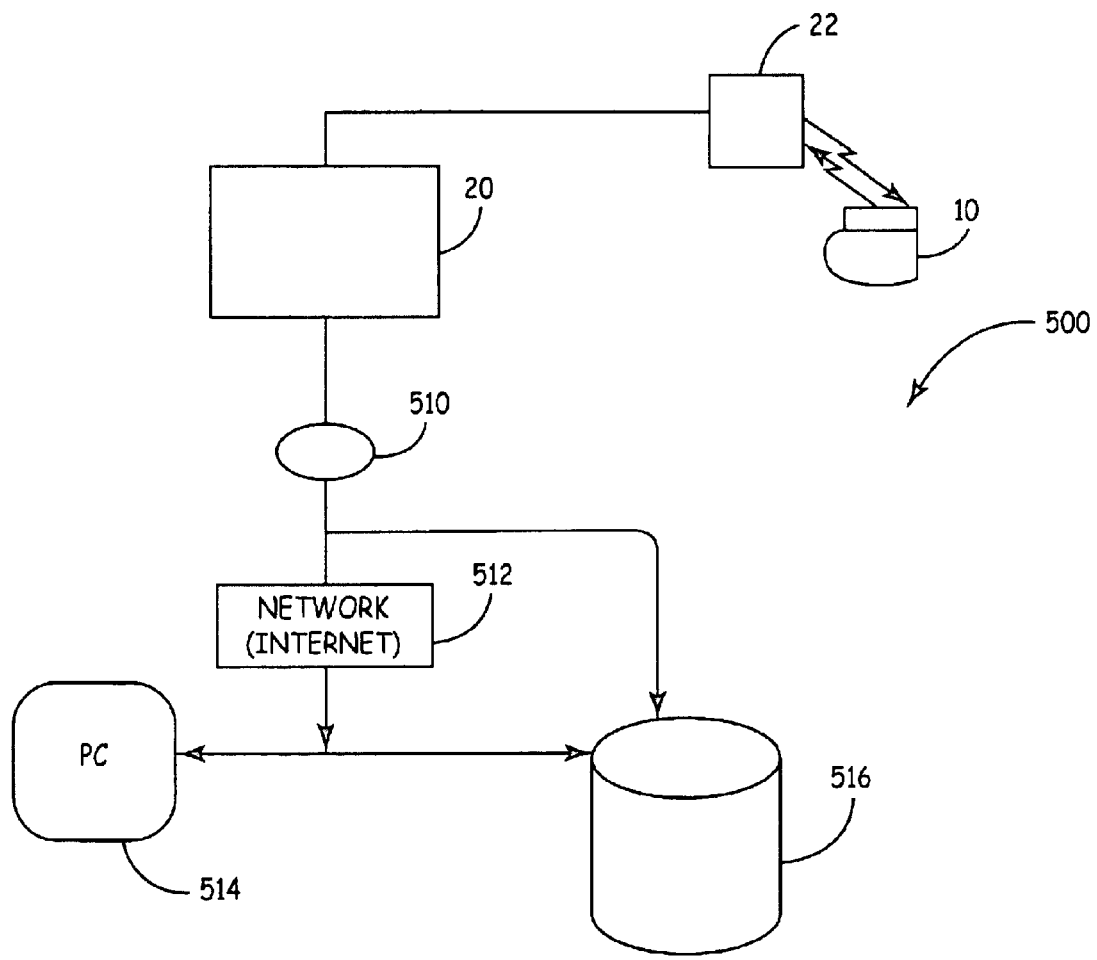
FIG. 9 is a block diagram representing data collection and measurement system using sensors in accordance with the present invention.

FIG. 9 is a representation of a data management system in which data collected using the sensors of the present invention is remotely transferred using a data transfer medium 510 such as, for example, but not limited to, a modem, cable, fiber optics or equivalent, via network system 512 to PC 514 at the remote station. The system also enables direct data archival in server 516. Generally, the system is structured to enable physicians and other healthcare providers to use their PC at remote locations to access and review patient physiologic data collected by sensors 230 (FIG. 5) via telemetry head 22, transferred and reviewed at programmer 20. The data from programmer 20 could be transferred as discussed hereinabove, for review at PC 514 and storage and retrieval at 516. In this manner, the system is capable to provide transtelephonic monitoring or Web-enabled remote patient management to promote chronic remote patient care.

While particular embodiments have been shown and described herein, it will be apparent to those skilled in the art that variations and modifications may be made in these embodiments without departing from the spirit and scope of this invention. It is the purpose of the appended claims to cover any and all such variations and modifications.

What is claimed is:

1. A system including a non-tissue contacting electrode in cooperation with an external device, the system comprising:
   an IMD in data communication with the external device; and
   means for establishing the data communication between said IMD and the external device;
   said means for establishing the data communication being adapted to incorporate the non-tissue contacting electrode wherein the non-tissue contact electrode includes sensing means to detect cardiac depolarization waveforms.

2. The system of claim 1 wherein said means for establishing the data communication includes a telemetry unit in operable data and electrical communications with the external device.

3. The system of claim 2 wherein said telemetry unit is a hand-holdable telemetry head adapted to be placed within a telemetry range of said IMD.

4. A system including a non-tissue contacting electrode in cooperation with an external device, the system comprising:
   an IMD in data communication with the external device; and
   means for establishing the data communication between said IMD and the external device;
   the non-tissue contacting electrode being adapted to communicate with said external device such that EKG readings from the electrode are displayable on said external device.

5. The system according to claim 4 wherein said external device is a programmer.

6. The system according to claim 4 wherein at least two electrodes are implemented to sense EKG signals.

7. The system according to claim 6, further including means for selecting larger signals among signals sensed from said at least two electrodes.

8. A non-contact electrode system having at least one electrode, the system comprising:
   means for adapting the least one of said non-contact electrode for attachment; and
   means for transferring physiologic data obtained by said at least one electrode to an external device.

9. The system of claim 8 wherein said at least one electrode includes attachment to a programmer head.

10. The system of claim 8 wherein said at least one electrode includes attachment to an electrode strip.

11. The system of claim 8 wherein said physiologic data includes respiration signal implemented to provide one of implantable medical device follow-up, emphysema, edema and CHF monitoring and AVD optimization.

12. The system of claim 8 wherein said physiologic data includes data obtained in cooperation with an implanted medical device wherein capture detection and ischemia detection are obtained for monitoring.

13. A non-contact electrode in cooperation with a Web-enabled data management system, comprising:
   means for transferring physiologic data collected from a patient with an implanted medical device (IMD);
   an external device in data communication with the non-contact electrode to uplink and transfer said physiologic data;
   interface means to transfer said physiologic data from said external device to a network; and
   means to transfer said physiologic data from said network to a PC or a network server.

14. The system of claim 13 wherein said network is Web-enabled and is remotely located from the electrode location.

15. The system of claim 13 wherein said interface is one of a modem, cable, fiber optics and RF.

16. A method of collecting physiological data using one or more non-contact electrodes comprising:
   positioning the one or more non-contact electrodes proximate to a patient; and
   transferring physiologic data collected by the electrodes to an external device.

17. The method of claim 16 wherein the electrodes are implemented with a telemetry head wherein said transfer of data includes telemetry communication with an implanted medical device.

* * * * *